(12) United States Patent  (10) Patent No.: US 9,374,950 B2
Upadhyaya et al.  (45) Date of Patent: Jun. 28, 2016

(54) SYSTEM AND METHODS FOR MONITORING LEAF TEMPERATURE FOR PREDICTION OF PLANT WATER STATUS

(71) Applicant: THE REGENTS OF THE UNIVERSITY OF CALIFORNIA, Oakland, CA (US)

(72) Inventors: Shrinivasa K. Upadhyaya, Davis, CA (US); Rajveer Dhillon, Davis, CA (US); Jedediah Roach, Sacramento, CA (US); Francisco Rojo, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 64 days.

(21) Appl. No.: 14/268,880

(22) Filed: May 2, 2014

(65) Prior Publication Data

US 2014/0326801 A1  Nov. 6, 2014

Related U.S. Application Data

(60) Provisional application No. 61/818,527, filed on May 2, 2013.

(51) Int. Cl.
  *G01N 33/24* (2006.01)
  *A01G 25/16* (2006.01)
  *A01G 1/00* (2006.01)

(52) U.S. Cl.
  CPC .............. *A01G 25/167* (2013.01); *A01G 1/001* (2013.01); *G01N 33/246* (2013.01)

(58) Field of Classification Search
  CPC ............ A01G 1/001; A01G 2013/002; A01G 13/0225; A01G 13/0206; A01G 25/167; G01N 33/246

USPC ........ 73/73; 47/21.1, 29.1; 239/11, 69; 702/2
See application file for complete search history.

(56) References Cited

U.S. PATENT DOCUMENTS 2,986,842 A * 6/1961 Toulmin, Jr ............ A01G 7/045
                                                     239/557
3,727,345 A * 4/1973 Smith ..................... A01G 13/06
                                                     239/269

(Continued)

FOREIGN PATENT DOCUMENTS

WO  WO 2010/117944  * 10/2010 ........... A01G 25/167

OTHER PUBLICATIONS

Christensen, J. "Low-Cost Anemometer Fights Dust," Nov. 2, 2001, Maximum Integrated Application Note 844, pp. 1-3.

*Primary Examiner* — Daniel S Larkin
(74) *Attorney, Agent, or Firm* — O'Banion & Ritchey LLP; John P. O'Banion (57) ABSTRACT

An apparatus and system for monitoring plant leaves to determine plant water needs and an automated variable-rate irrigation management system which can implement precision irrigation by taking into account specific plant water status is presented. Single or networked sensor platforms have a suite of sensors including a leaf temperature sensor for measuring leaf temperatures over time; an air temperature sensor; a relative humidity sensor for measuring relative humidity surrounding a leaf; a wind speed sensor for measuring wind speed surrounding a leaf; and an ambient light sensor for measuring solar radiation on the leaf. One platform has diffuser dome, leaf retainer and wind barrier structures. The sensor platform may have a computer processor and programming for obtaining and recording sensor measurements and determining plant water status in response to sensor measurements. The system may have a central control computer and communications link for communications with the platforms.

28 Claims, 7 Drawing Sheets

(56) References Cited

U.S. PATENT DOCUMENTS

| | | | | |
|---|---|---|---|---|
| 4,209,131 A * | 6/1980 | Barash | A01G 25/16 | 137/624.2 |
| 4,755,942 A * | 7/1988 | Gardner | A01G 25/16 | 47/1.01 R |
| 4,763,440 A * | 8/1988 | James | A01G 13/0206 | 47/2 |
| 4,876,647 A * | 10/1989 | Gardner | A01G 25/16 | 700/284 |
| 4,998,826 A * | 3/1991 | Wood | A01G 7/00 | 250/334 |
| 5,423,148 A * | 6/1995 | Thornhill | A01G 9/12 | 47/29.1 |
| 5,539,637 A * | 7/1996 | Upchurch | G05D 22/02 | 700/284 |
| 5,605,008 A * | 2/1997 | Johnston | A01G 13/04 | 47/29.2 |
| 6,397,162 B1 * | 5/2002 | Ton | A01G 7/00 | 702/136 |
| 6,597,991 B1 * | 7/2003 | Meron | A01G 25/167 | 382/110 |
| 6,701,665 B1 * | 3/2004 | Ton | A01G 1/00 | 47/17 |
| 2002/0170229 A1 * | 11/2002 | Ton | A01G 7/00 | 47/1.7 |

* cited by examiner

SYSTEM AND METHODS FOR MONITORING LEAF TEMPERATURE FOR PREDICTION OF PLANT WATER STATUS

CROSS-REFERENCE TO RELATED APPLICATIONS

This application claims priority to, and the benefit of, U.S. provisional patent application Ser. No. 61/818,527 filed on May 2, 2013, incorporated herein by reference in its entirety.

STATEMENT REGARDING FEDERALLY SPONSORED RESEARCH OR DEVELOPMENT

This invention was made with Government support under SCRI-2010-01213 awarded by the United States Department of Agriculture. The Government has certain rights in the invention.

INCORPORATION-BY-REFERENCE OF COMPUTER PROGRAM APPENDIX

Not Applicable

BACKGROUND

1. Technical Field

This disclosure pertains generally to agricultural sensors and plant status detection schemes, and more particularly to an apparatus and system of sensors and methods that monitor leaf temperature and corresponding microclimatic conditions in real-time and produce a reliable plant water status indicator. The sensor system can be integrated with a wireless network to continuously monitor the plant water stress status and control an automated variable-rate irrigation management system. It can also be used as a standalone unit to record plant water status continuously.

2. Background Discussion

The aim of irrigation scheduling for crops is to maximize water use efficiency, to maximize yield and to reduce the overall demand on water resources. Current practices of irrigation scheduling followed by growers are mostly based on the condition of the crop and the feel of the soil. Automatic irrigation scheduling techniques developed over the years usually monitor "soil moisture content" or "soil water balance" and uses that information to make decisions regarding irrigation events. Even though the soil monitoring approach to irrigation scheduling has been found to be fairly successful in field crops that have a relatively shallow root zone as compared to tree crops, the approach is problematic because it ignores the physiological responses of the plants to changing environmental conditions. The soil moisture content does not represent the available water to plants, especially tree crops that have a vast root system, as the moisture measurement using a soil moisture sensor indicates the available moisture at the location of the sensor rather than for the whole root zone.

Because plants respond directly to changes in the water status of their tissues, sensing plant water stress has been considered to be a better indicator of irrigation requirements than monitoring soil water content. Various tools have been used to measure plant water stress for irrigation scheduling purposes. Using a pressure chamber is the most common method of measuring stem water potential (SWP) for tree crops. Although mid-day SWP measurements taken by a pressure chamber are considered as the standard method, it is a very time consuming and labor intensive procedure. This makes it an impractical technique for development of an efficient precision irrigation scheduling system that requires frequent and high density spatial SWP data collection.

Thermal sensing is also a promising technique used to sense plant water stress by measuring canopy temperatures using infra-red thermometers (IRT) or thermal cameras. Stomates of any healthy plant that is not under water stress tend to open fully when exposed to sunlight, which in turn increases transpiration. The evaporation of water through the leaf stomata during the transpiration process cools the leaf surface, which is an indicator of the extent of opening or closing of the leaf stomata. Therefore, differences in leaf temperatures compared to ambient temperatures have been studied to determine the water stress level of plants.

Crop water stress index (CWSI) is one of the most commonly used indices used to quantify plant water stress for irrigation management. However, it has been found that it requires extensive measurements in a wide range of vapor pressure deficit (VPD) conditions to obtain meaningful values of CWSI. It can also be sensitive to environmental factors like wind and PAR creating inaccuracies.

Accordingly, there is a need for a system and method for evaluating crop water status that makes taking extensive measurements over a wide range of VPD for calculating meaningful values of stress indices (e.g. CWSI) inexpensive, quick and easy.

SUMMARY

We have developed a "Leaf Monitor" sensor system and methods that can monitor leaf temperature and the corresponding microclimatic conditions in real-time. Thermal sensing of a leaf also has the advantages of being non-destructive, noncontact, inexpensive, convenient to use, and easy to automate as compared to other methods, which make it a good technique to use for monitoring plant water stress in field or orchard environments.

A key feature of the apparatus and methods accounts for spatial variability of plants within an orchard or vineyard by evaluating the plant water stress status of an individual or a block of trees. Moreover, it utilizes the sensor data obtained immediately following an irrigation event (i.e., first or second day following an irrigation) to develop a saturation baseline specific to that irrigation event to account for temporal variability during the season. Since this sensor suite is capable of accounting for both spatial and temporal variability in crop water stress index, the term ST-CWSI is used to denote stress status derived from the unit.

The sensing system can be used as an irrigation scheduling tool as it is able to provide daily stress index value which follows a similar pattern as the actual plant water stress since the spatio-temporal crop water stress index (ST-CWSI) values were found to be highly correlated with measured plant water stress. Furthermore, leaf temperature data captured throughout the season can account for any seasonal changes in the tree's response to stress level.

The system sensor platforms can be installed on orchard trees to continuously monitor a selected leaf on each tree by logging leaf temperature, air temperature, relative humidity, wind speed and Photosynthetically Active Radiation (PAR). Leaf monitors can be installed in orchards as individual units or as part of a wireless mesh network. The sensor data can also be accessible over the web. Furthermore, such a leaf monitor can be easily integrated with an automated variable-rate irrigation management system which can implement precision irrigation by taking into account plant water status.

The structural design of the leaf monitor also assists in controlling levels of disturbance variables like wind speed and light conditions. Leaf-monitor data acquired from different trees can be filtered for a particular time window of the day. Continuous measurements of leaf temperature and microclimatic parameters can also address the problem of taking extensive measurements over a wide range of VPD for calculating meaningful values of stress indices (e.g. CWSI) seen in current approaches.

One preferred embodiment of the apparatus utilized for monitoring plant leaves to determine plant water needs, has a leaf holder configured for retaining at least one leaf of a tree or other plant in fixed position. In this embodiment, the leaf holder is formed from a first and second mesh regions that retains the leaf sandwiched between the mesh regions. The apparatus also has a sensor suite and a computer processor configured to receive measurement information from the sensor suite and computing the plant water status from the sensor data.

In one embodiment, the sensor suite includes: (i) an infrared thermometer (IRT) for periodically or continuously measuring the temperature of the leaf; (ii) an air temperature sensor; (iii) a relative humidity sensor for measuring the relative humidity surrounding the leaf; (iv) a wind speed sensor for measuring wind speed around the leaf; and (v) an ambient light sensor that measures levels of solar radiation on the leaf. The infra-red thermometer (IRT) of the sensor suite may be positioned in a substantially normal position, or perpendicular, to the surface of the leaf.

In one embodiment, the plant water status (PWS) is determined by (1) continuously recording measurements from the sensor suite during each day after plant irrigation associated with the leaf being monitored; (2) smoothing the sensor data with a moving average after filtering out unusual values; (3) performing regression analysis of the data to develop a functional relationship between leaf temperature, air temperature, leaf light level, the slope of the saturated vapor pressure-temperature relation curve, and the Vapor Pressure Deficit (VPD) following an irrigation event to develop an equation for the saturation condition; and (4) determining plant water stress levels for each data point during the rest of the days following the irrigation event until the occurrence of the next irrigation event.

The system apparatus may also have a wind barrier for suppressing effects of wind speed on leaf transpiration. The wind speed sensors can be positioned inside and outside of the wind barrier to detect and verify effectiveness of the wind barrier.

The apparatus may also comprise a solar radiation diffuser, adapted for directing light upon the leaf with a uniform light level. For example, the solar radiation diffuser can be an opaque material with a convex or hemispherical shape retained over, or surrounding, the leaf that is intended to provide more uniform light conditions for the data analysis.

In another embodiment, the programming executable on the processor determines the plant water stress level in response to the monitored environmental parameters in the vicinity of the leaf and the leaf temperature on a continuous basis.

Monitoring of the sensors can be continuous or the sensor data acquisition can be periodic at random or predetermined time intervals. One embodiment includes a real-time clock configured for (i) awakening the processor for obtaining sensor readings; or (ii) storing a value generated by the real-time clock along with storing the of the measurements; or (iii) both awakening the computer processor and storing the value generated by the real-time clock along with storing each measurement.

Information regarding the leaf temperature and environmental parameters can be stored in a memory such as a non-volatile memory card or a volatile memory on the processor. The data can also be transmitted to a central computer for processing or storage. This embodiment has a wireless transmitter and/or transceiver that is operably coupled to the computer processor that is capable of communicating wireless data to and from networked system computers regarding plant water needs and irrigation needs. For example, a central system computer receives measurement information from the sensor suite of the devices and the plant water status is determined from the measurement information. The central computer controls specific irrigation devices in response to the plant water status. Alternatively, irrigation devices may be controlled by the processor and programming of a single device without an established network.

According to one aspect of the technology, a sensor system is provided that senses leaf temperatures and air temperature, relative humidity, wind speed and ambient light surrounding the leaf.

According to another aspect of the technology, an apparatus and method are provided that calculates plant water stress level and watering needs from monitored leaf temperature sensor data.

Another aspect of the technology is to provide a system for selective water distribution based on the calculated needs of the plants determined from sensor data.

According to another aspect of the technology, a sensor device or network of sensor devices are provided that will continuously monitor plant water status and actuate and control irrigation devices in response to plant water status.

According to another aspect of the technology, a method is provided for production of a spatio-temporal crop water stress index (ST-CWSI) where a reference baseline from well watered plants is developed after every irrigation event for each tree or a block of trees for incorporating any temporal variability throughout the season.

A further aspect of the technology is the potential application of the system as an inexpensive weather station since it can provide data such as wind speed, ambient light, temperature, and relative humidity.

Further aspects of the technology will be brought out in the following portions of the specification, wherein the detailed description is for the purpose of fully disclosing preferred embodiments without placing limitations thereon.

BRIEF DESCRIPTION OF THE SEVERAL VIEWS OF THE DRAWINGS

Our technology described herein will be more fully understood by reference to the following drawings which are for illustrative purposes only.

DETAILED DESCRIPTION

Referring more specifically to the drawings, for illustrative purposes an embodiment of the apparatus and method for producing a crop water stress index of a plant that will allow general irrigation scheduling and plant based plant or site-specific irrigation is described and depicted generally in FIG. 1 through FIG. 4. It will be appreciated that the methods may vary as to the specific steps and sequence and the apparatus may vary as to elements without departing from the basic concepts as disclosed herein. The method steps are merely exemplary of the order in which these steps may occur. The steps may occur in any order that is desired, such that it still performs the goals of the claimed technology.

Figure 1:
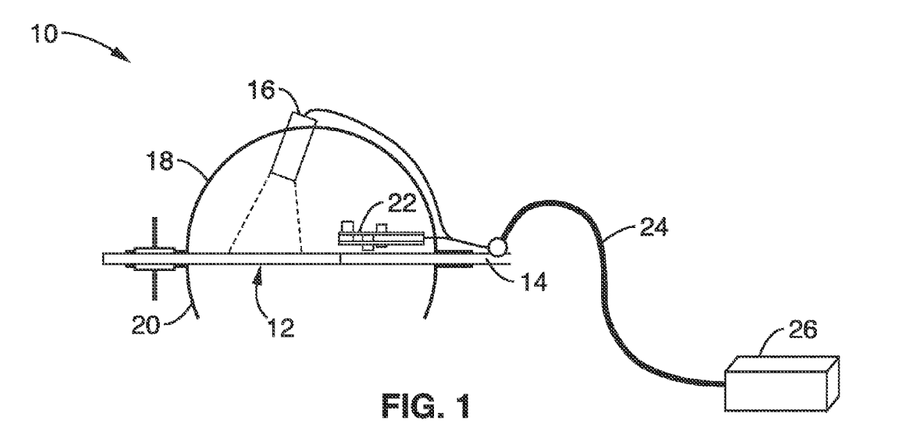
FIG. 1 is a schematic side sectional view of a leaf monitoring apparatus according to one embodiment of the technology.

The preferred single unit leaf monitor apparatus 10 is shown schematically in FIG. 1. The monitor 10 can stand alone or can be connected to a network of monitors throughout an orchard or field with network control. The monitor 10 platform is attached to at least one leaf 12 that is connected to a branch of the subject tree.

The leaf 12 is preferably secured in a leaf holder 14 so that it is properly oriented for the sensors so that measurements can be made continuously or periodically over time. For example, the leaf holder 14 ensures that the selected leaf 12 is fixed in front of the leaf temperature sensor 16 so that that the sensor is consistently looking at leaf surface in order to make continuous leaf temperature measurements. Leaf 12 is also completely covered inside of dome 18 and securely fixed by leaf holder 14 in front of the leaf temperature sensor 16. The leaf holder 14 embodiment of FIG. 1 basically consists of mesh made of nylon wire secured around two metal rings. Leaf 12 is held between these two rings by the nylon wire and the position of rings can be adjusted according to leaf orientation.

Because the leaf 12 may be exposed to non-uniform solar radiation, a solar radiation diffuser dome 18 covers the leaf 12 to ensure that the light sensors are exposed to the same light levels as the leaf. The diffuser 18 has a hemispherical opaque plastic film that diffuses direct sunlight flecks to essentially provide uniform light conditions inside the dome. Although a dome shaped diffuser cover 18 is shown in FIG. 1, the diffuser cover need not be of any particular shape.

The open bottom of the diffuser dome 18 includes a wind barrier 20 to reduce wind effects. The wind barrier 20 generally has the same diameter as the diffuser dome 18 and is typically mounted to the opening of the leaf holder frame 14. The wind barrier 20 may have tapered walls that are preferably made from a transparent material. The sensitivity and reliability of the leaf monitor sensors are improved in the system because of the presence of the wind barrier 20 around the leaf 12 that eliminates wind speed as a factor.

In one embodiment, the wind speed sensors are positioned both inside and outside of the wind barrier 20 to detect and verify the effectiveness of the wind barrier 20 for suppressing the effects of wind speed on the plant stress measurements. Wind sensors should be sensitive at low wind speeds as low wind conditions are expected around the leaf when a wind barrier is in place.

A sensor suite 22 is preferably placed in the interior of the diffuser dome 18 to monitor conditions surrounding the leaf. The sensor suite 22 preferably includes a microcomputer that is interfaced with the various sensors such as: (i) a leaf temperature sensor such as an infra-red thermometer (IRT) 16 for measuring the temperature of the leaf, (ii) an air temperature thermometer, (iii) a relative humidity sensor configured for measuring air temperature and relative humidity proximal to the leaf, (iv) a wind speed sensor configured for measuring wind speed proximal to the leaf, and (v) an ambient light sensor configured for measuring levels of solar radiation on the leaf.

The individual sensors of the sensor suite 22 are coupled to a control box 26 with a cable or cables 24 in the embodiment of FIG. 1. The control box 26 can be a data storage unit integrated with the sensor suite 22 microcomputer or it can be a wireless node.

If the control box 26 is integrated with the microcomputer and provides data storage, a power supply subsystem with batteries or a solar panel for power generation may be provided within the control box 26 to provide power for sensor suite 22.

If control box 26 is a wireless node, it may additionally include a wireless transmitter, or transceiver, coupled to the computer processor that is configured for communicating data wirelessly to a remote device or network server computer. In one embodiment, the control box 26 transmits sensor data to a remote computer where it is uploaded to the web so that it can be accessed remotely as well. Irrigation initiation in this embodiment is controlled by the remote computer rather than by the processor in the field platform. In another embodiment, the irrigation is controlled by the control box 26 or platform processor but the irrigation initiation signal is created in the remote computer. The individual field platforms are part of a wireless network controlled by a remote computer in this instance.

The leaf monitor apparatus 10 may be configured to continuously take sensor readings at set intervals over a period of a day or over many days. In one embodiment, the leaf monitor apparatus 10 has a real-time clock that awakens the processor for obtaining sensor readings; or stores a value generated by the real-time clock along with the stored measurements; or both awakens the computer processor and stores the value generated by the real-time clock along with storing each measurement.

Measurement data storage can be either permanent or transferrable with the use of removable memory or media. In another embodiment, the control box 26 with a wireless node can transmit data wirelessly to a remote computer where it can be stored, uploaded to the web or processed remotely.

Figure 2:
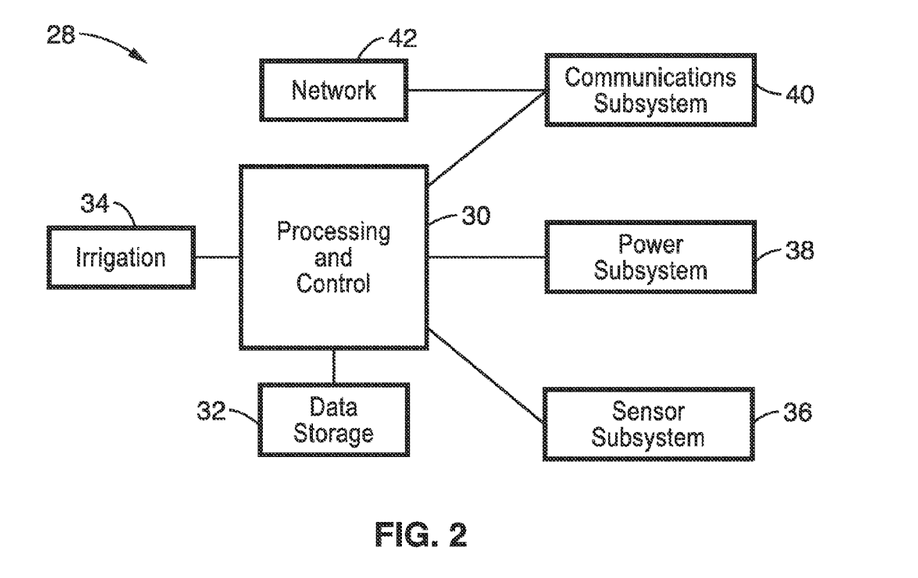
FIG. 2 is a block diagram of apparatus subsystems of one embodiment of the technology.

The preferred subsystems 28 of the apparatus platform of FIG. 1 are shown schematically in FIG. 2. This embodiment of the apparatus can be easily integrated with an automated variable-rate irrigation management system which can implement precision irrigation by taking into account plant water status. Alternatively, the grower may use the system to provide uniform irrigation over a large area based on the apparatus measurements. In this case, only one leaf monitor is used to predict irrigation needs for a section of a field, orchard, or large area.

At the core is the processing and control subsystem 30 that can range in sophistication from a programmable microcontroller to a computer microprocessor. The processing and control subsystem 30 may also have data storage capabilities. Data storage 32 can be a conventional removable flash drive or micro SD card or a permanent part of the control box. A real-time clock and alarm may also be part of the processing and control subsystem 30.

In the embodiment shown in FIG. 2, the processing and control subsystem 30 is connected to an irrigation control system 34 or individual valve control for irrigation of a specific tree or a group of plants. There are many different types of irrigation systems known in the art. Generally, the processing and control subsystem 30 initiates a signal to the irrigation control to open and close valves so that a desired volume of water is applied to a tree. The frequency and duration of valve actuation and the time of day can also be determined by the processing and control subsystem 30. The programming of irrigation events incorporates the results of sensor data from specific plants or trees.

The processing and control subsystem 30 is also associated with the sensor subsystem 36, the power subsystem 38 and the communications subsystem 40. The sensors of the sensor subsystem 36 are selected to provide continuous or periodic measurements of leaf temperature (TL), air temperature (TA), ambient light (Rn), relative humidity (RH) and wind speed (u). Although these sensors are preferred, it will be seen that other sensor types can be substituted or incorporated into the sensor subsystem 36.

Sensor data is collected, processed and recorded and calculations may be performed by programming of the processing and control subsystem 30. Calculations and processing of collected sensor data may also be performed outside of the sensor platform by a network computer system 42. In one embodiment, the data collected from the suite of sensors is filtered by the programming of the apparatus processing and the control subsystem 30 as part of the plant water status (PWS) determination. For example, the programming of the field platform 10 may filter the data from the sensor suite to utilize only data corresponding to a specific time window of the day.

The power subsystem 38 provides electrical power to the sensors and other subsystems for their operation. The platform is preferably self-contained with batteries. The power subsystem 38 may also include a power generation scheme such as solar cells or wind generation. The power subsystem 38 monitors the power levels and may also include an alarm function when power levels dip below a pre-determined threshold.

The communications subsystem 40 is optional and is used in embodiments where remote communications with a monitoring computer or a network control computer 42 are desirable. In the embodiment of FIG. 2, the communications subsystem 40 is connected to a network control 42 that can be connected with many other monitor platforms within an orchard, for example.

In one embodiment, the network control computer monitors the sensor data and crop water stress calculations of all of the platforms in the network to allow a geographical assessment of the water needs of the orchard as a whole with the status of selected trees. Irrigation and timing trends can be compiled and used for water use planning.

In another embodiment, the network control computer 42 can communicate with the platform processing and control 30 subsystem through the communications subsystem 40 to receive raw and stored sensor data and perform the crop water stress calculations remotely and then return instructions to the monitor platform for initiating irrigation events.

In an alternative embodiment, the actuation of the irrigation system 34 is determined by the individual platform and control 30, but platform control may be overridden by the network control computer 42 with a signal through the communications subsystem 40. For example, the actuation of the irrigation system 34 may be delayed to a later time or the total volume of water delivered could be changed by changing the duration and frequency of the valve openings by the network control computer 42.

Figure 3:
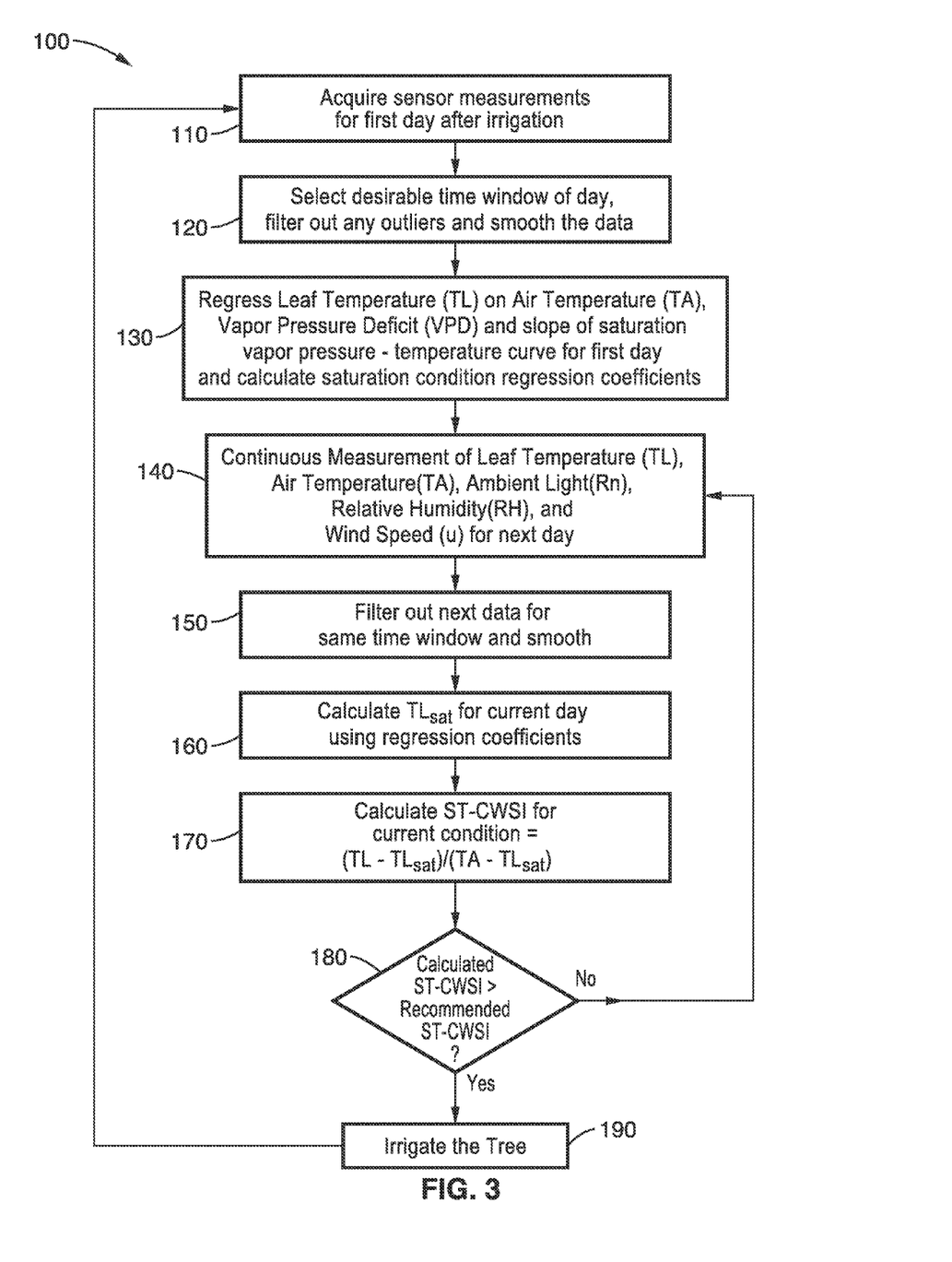
FIG. 3 is a schematic flow diagram of one method for determining a Spatio-temporal Crop Water Stress Index and plant specific watering needs.

Turning now to FIG. 3, a flow diagram of one embodiment of a method 100 for generating a spatio-temporal crop water stress index (ST-CWSI) for a specific tree is generally shown. As seen in FIG. 2, the recording and calculation steps are normally performed by the processing and control subsystem 30 programming or may be performed by a network computer 42 through the communications subsystem 40. In the embodiment shown in FIG. 3, the process begins with periodic or continuous measurements of leaf temperature (TL), air temperature (TA), ambient light (Rn), relative humidity (RH) and wind speed (u) for a period of time after irrigation at block 110.

At block 120, a time window is selected and the sensor data within that window for that day is smoothed with a moving average after filtering out unusual values.

At block 130 of FIG. 3, a relationship between leaf temperature (TL), air temperature (TA), ambient light (Rn), vapor pressure deficit (VPD) and the slope of the saturation vapor pressure curve for first day is developed for calculating saturation conditions for use during the rest of the days after that irrigation event. The leaf temperature (TL) on air temperature (TA), vapor pressure deficit (VPD) and slope of saturation vapor pressure-temperature curve for first day are regressed and the saturation condition regression coefficients are calculated at block 130.

On the next day after the irrigation period, the measurements of leaf temperature (TL), air temperature (TA), ambient light (Rn), relative humidity (RH) and wind speed (u) are regularly taken at block 140. The acquired data at block 140 is filtered and smoothed with a moving average out at block 150.

At block 160, the saturation leaf temperature (i.e. $TL_{sat}$) corresponding to each data point is calculated using the relationship developed in block 130.

The spatio-temporal crop water stress index (ST-CWSI) is then calculated at block 170 for each data point (TL) using the formula: $(TL-TL_{sat})/(TA-TL_{sat})$. It is also assumed for a shaded, non-transpiring leaf that $TL_{dry}=TA$, in this particular embodiment. Better estimates of $TL_{dry}$, that accounts for light level, can also be implemented here in other embodiments.

Decision block 180 requires a comparison of the calculated (ST-CWSI) with the recommended (ST-CWSI) from a standard table. If the calculated (ST-CWSI) value is greater than the recommended (ST-CWSI) value then the tree is irrigated at block 190. Normally a signal is generated to open the irrigation valve for a set period. The ST-CWSI generated will also be used for determining the duration of irrigation. However, the availability of water restricts when an orchard can be irrigated (i.e., if a grower has a fixed schedule), then ST-CWSI signal will provide the feedback signal to determine the amount of water that should be applied. In another embodiment, the larger the difference between the calculated and recommended (ST-CWSI), the longer the duration of the irrigation event at block 190 representing a higher crop coefficient.

If the calculated (ST-CWSI) value is less than the recommended (ST-CWSI) value, then the sensor measurements continue to be evaluated and recorded and there is no irrigation event initiated at block 190. The procedure will continue again with the steps from block 140 to block 190.

If the irrigation system activation was initiated at block 190, then the procedure will start again from block 110 and new saturation data will be acquired for developing a new saturation line.

Since the ST-CWSI is calculated for a specific tree or site and the saturation baseline for the calculation of CWSI is updated after every irrigation event, the apparatus can account for both spatial and temporal variability in plant water stress throughout the orchard and throughout the course of the season.

Figure 4:
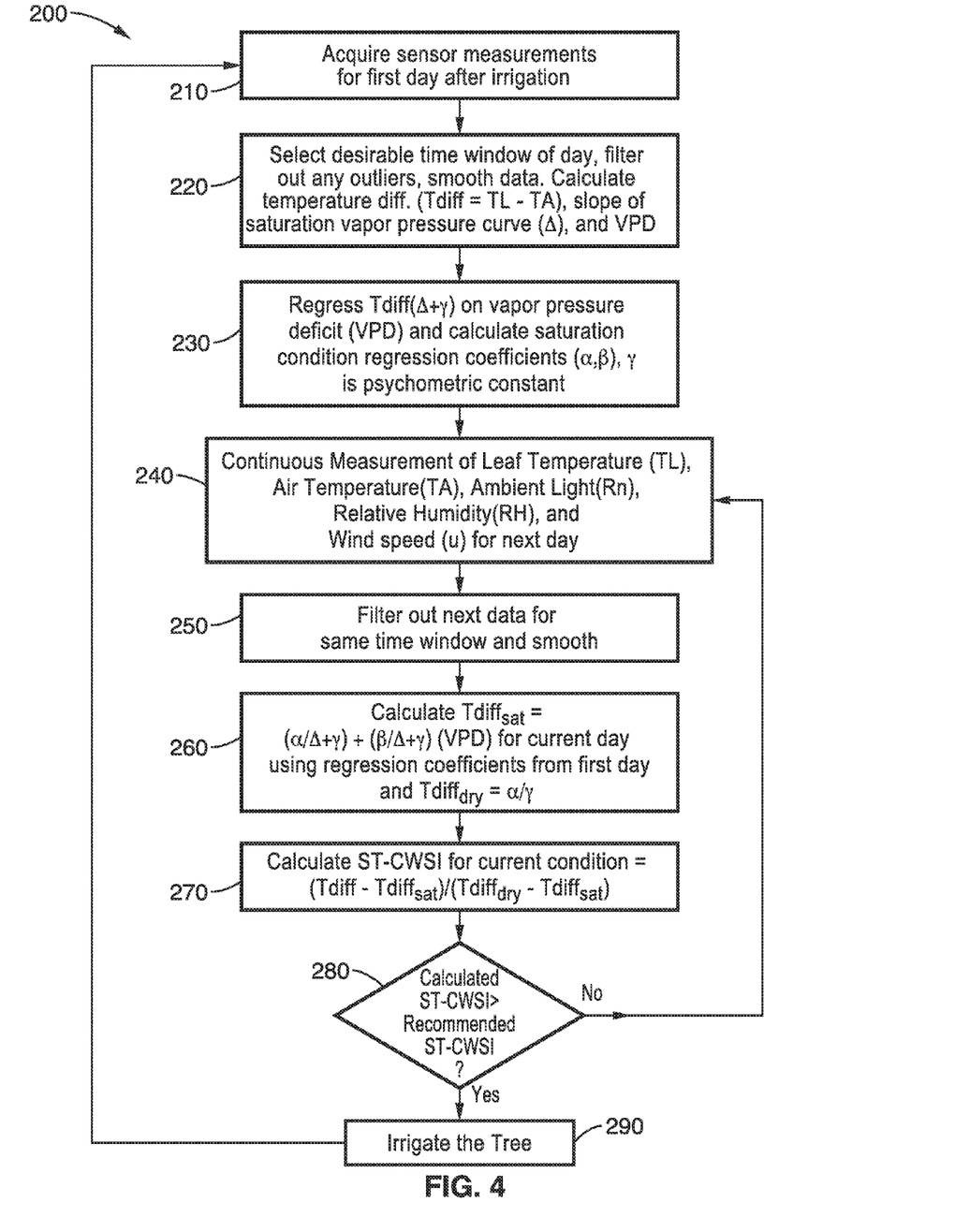
FIG. 4 is a schematic flow diagram of an alternative method for determining a Spatio-temporal Crop Water Stress Index and plant specific watering needs.

Turning now to FIG. 4, a flow diagram of an alternative method 200 for generating ST-CWSI values for a specific tree is generally shown. In the embodiment shown in FIG. 4, the process begins with periodic or continuous measurements of leaf temperature (TL), air temperature (TA), ambient light (Rn), relative humidity (RH) and wind speed (u) for a period of time after irrigation at block 210. The acquired sensor measurements at block 210 can be recorded or processed in real-time.

At block 220 of FIG. 4, the temperature difference (Tdiff=TA−TL), the slope of saturation vapor pressure curve ($\Delta$), ambient light level (Rn), and the vapor pressure difference (VPD) for all data points are calculated. A time window is selected and any outlier data are preferably filtered and the data is smoothed mathematically.

The slope ($\beta$) and intercept ($\alpha$) are calculated at block 230 by regressing Tdiff ($\Delta$+$\gamma$) on VPD, where $\gamma$ is psychometric constant (Pa/° C.). The $\beta$ can be assigned as the slope for the saturation condition. It is also assumed for a shaded, non-transpiring leaf that $Tdiff_{dry} = \alpha/\gamma$.

On the next day of the post-irrigation period, the measurements of leaf temperature (TL), air temperature (TA), ambient light (Rn), relative humidity (RH) and wind speed (u) are regularly taken at block 240.

At block 250 of FIG. 4, the temperature difference (Tdiff=TA−TL), $\Delta$, and the VPD for all data points are calculated.

At block 260, the saturation Tdiff, (i.e. $Tdiff_{sat}$) corresponding to each data point (VPD) is calculated using the $\alpha$ and $\beta$ that were calculated from the first day measurements. The calculated $Tdiff_{sat}$ value is: $Tdiff_{sat}$ ($\Delta$+$\gamma$)=$\alpha$+$\beta$(VPD). The $Tdiff_{dry}=\alpha/\gamma$.

The ST-CWSI is calculated for each data point (Tdiff) using the formula: $(Tdiff-Tdiff_{sat}/Tdiff_{dry}-Tdiff_{sat})$. The mean and standard deviation of ST-CWSI may also be calculated and evaluated at block 270.

Decision block 280 requires a comparison of the calculated ST-CWSI with the recommended ST-CWSI from a standard table. If the calculated ST-CWSI value is greater than the recommended ST-CWSI value then the tree is irrigated at block 290. Normally a signal is generated to open the irrigation valve for a set period. However, in one embodiment, the larger the difference between the calculated and recommended ST-CWSI, the longer the duration of the irrigation event at block 290.

If the calculated ST-CWSI value is less than the recommended ST-CWSI value, then the sensor measurements continue to be evaluated and recorded at block 240 and there is no initiation of an irrigation event at block 290.

If irrigation was initiated at block 290, then the procedure will start again from block 210 onward and new saturation data will be acquired for developing a new saturation line.

As ST-CWSI is a tree or site specific calculation and the saturation baseline for the calculation of CWSI is updated after every irrigation event, the method can account for both spatial and temporal variability in plant water stress throughout the orchard and throughout the season.

Our technology may be better understood with reference to the accompanying examples, which are intended for purposes of illustration only and should not be construed as in any sense limiting the scope of the claims appended hereto.

Example 1

In order to demonstrate the functionality of our technology, a sensor system for measuring leaf temperature and environmental parameters in the vicinity of a leaf on a continuous basis to detect plant water status was constructed. In this illustration, the sensor system used an infra-red thermometer (IRT) to measure leaf temperature, a temperature and relative humidity sensor to measure air temperature and relative humidity around the leaf, a wind speed sensor to measure wind speed around the leaf, and an ambient light sensor to measure level of solar radiation on the leaf surface.

These sensors were assembled on a customized PC board along with an Arduino compatible microcontroller that could continuously monitor all the sensors at a desired sampling rate and report the data to a wireless node.

The apparatus included a leaf holder, a solar radiation diffuser dome, and a wind barrier. The leaf holder, which held a leaf in front of the IRT, was a mesh of nylon wire mounted around two metal rings. The leaf was held between the two rings and the position of the rings could be adjusted according to leaf orientation.

A solar radiation diffuser dome was also mounted on the leaf to reduce the effect of sun flecks illuminating the leaf thereby assuring uniform light level inside the dome. It had been noted previously that the surface of leaf under observation received non-uniform solar radiation at times. To make sure that light sensor was exposed to the same light level as the leaf, a solar radiation diffuser was mounted on the leaf. This diffuser was a hemispherical opaque plastic film which diffused direct sunlight flecks and made more or less uniform light conditions inside the dome.

A wind barrier was also installed as part of the dome to suppress the effect of wind speed on the transpiration of the leaf under observation. A wind speed sensor was installed inside the wind barrier to verify its effectiveness. The air temperature and humidity sensor and ambient light sensors were also mounted in parallel to the dome and close to the leaf surface. The IRT sensor was installed normal to the leaf surface from above.

The infra-red thermal sensor that was used was a Melexis MLX90614 non-contact infra-red thermometer that was positioned over the leaf to regularly measure leaf temperature. The sensor consisted of an IR sensitive thermopile detector chip, signal conditioning unit, 17-bit ADC. This sensor had a measurement resolution of 0.01° C. and an accuracy of 0.5°

C. The sensor was easy to interface with over the I2C communication bus and could operate on a 3 V or 5V DC power supply.

The temperature and humidity sensor was a MD0530 Temperature and relative humidity sensor from Modern Device. This digital sensor was an Arduino-compatible board which carries chip SHT21 for humidity and temperature measurements. It consisted of a capacitive humidity sensor, a band gap temperature sensor, a 14 bit ADC, and a 2 wire I2C protocol. It had 0.03% RH and 0.01° C. temperature resolutions and its corresponding tolerances were ±3% RH and less than ±0.5° C.

A low cost MD0550 analog wind sensor from Modern Device was used to measure wind speed around the leaf. This sensor was based on the hot-wire anemometer principle, where an element is heated up to a constant temperature and then the input electrical power was measured to maintain the heated element at a constant temperature when air flows over it. This sensor input powers with wind speed changes and is more sensitive at low wind speeds, a condition that exists around the leaf in this system because of the presence of the wind barrier around the leaf. Supply voltage can vary from 4-10 V and the output analog signal can be read by the Arduino board.

Additionally, an ambient light sensor, board JL0525 called "Lux plug" from Modern Device, was used to measure the ambient light around the leaf. This digital sensor consisted of the TSL2561 light sensor, a 16 bit ADC, and an I2C communication bus. The sensor had two photodiodes i.e. visible and IR, and IR only. Corresponding outputs from both photodiodes can read from separate channels and the sensor was calibrated and programmed to report light in units of LUX as well.

The leaf monitor platform was integrated into a wireless sensor network at the field site using wireless nodes. These wireless nodes were available commercially. An RS485 module installed on the leaf monitor PC board made it possible to communicate with the wireless sensor nodes. These nodes transmitted the sensor data to a gateway computer, a field computer, or a hub which in turn uploaded the data to the internet so that the data could be viewed from anywhere using a web browser. These wireless nodes typically use a solar panel to generate the required power and can easily power the leaf monitor sensors. This demonstration established that sensor data can be accessed remotely.

Example 2

In another demonstration, an Arduino compatible microcontroller—Seeeduino Stalker v2 (ARD04D2P, Shenzhen, China) was programmed to interface with all the sensors to record data continuously within a pre-determined time interval on a SD card installed in the microcontroller.

The selected microcontroller was used to program sensors and to record the data. Similar sensors and other leaf monitor components were used in this example as well. The selected board had an Atmega328 microcontroller, real-time clock, micro SD card, and an I2C pin header that allowed the board to be used as a data logger. The microprocessor board can be powered by rechargeable 3.6V lithium ion batteries and also has a circuit to charge the batteries using a solar panel.

The apparatus of Example 1 and Example 2 was tested on walnut and almond crops during the 2012 and 2013 growing seasons. The monitor was installed on shaded leaves to record measurements of leaf temperature, air temperature, relative humidity, ambient light, and wind speed continuously at one-minute intervals based on prior results that confirmed that shaded leaves can be used to detect plant water status.

Sensor data was obtained and recorded daily over a period of days. The differences between the air temperature and leaf temperature were evaluated. It was observed that leaf temperatures are approximately equal to air temperatures at night time and as the sun rises the leaf starts transpiring which results in a decrease in the leaf temperature with respect to air temperature. This temperature difference peaks at mid-day. Mid-day stem water potential (SWP) was also measured using a standard pressure chamber technique for the same tree to provide ground truth data.

Figure 5:
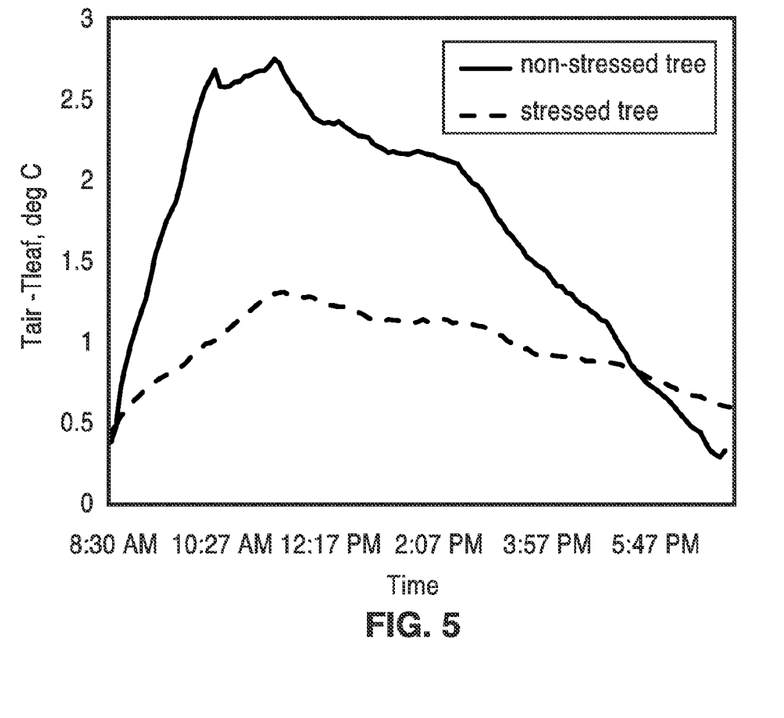
FIG. 5 is a graph of temperature difference ($T_{air}-T_{leaf}$) measured by a leaf monitor apparatus installed on two walnut trees treated with different irrigation levels.

FIG. 5 shows the data collected from two trees simultaneously at different plant water statuses. The plot shows that at mid-day a non-stressed tree leaf is cooler than a stressed tree leaf in comparison to the air temperature. Temperature difference ($T_{air}-T_{leaf}$) measured by the monitor installed on two walnut trees treated with different irrigation levels. The mid-day stem water potential (SWP) measured for stressed and non-stressed trees were −9.1 and −5.3 bars respectively.

Example 3

The sensor data from the apparatus was also used to demonstrate the detection of plant water status. Transpiration from the leaf surface and the associated leaf temperature depends not only on plant water status but also on several other environmental factors. For a given plant water status, transpiration also depends heavily on sunlight, vapor pressure deficit (VPD) and the wind speed levels at the leaf surface. It is therefore important to minimize the effect of these parameters to provide reliable plant water status indications.

As mentioned previously, a wind barrier was mounted around the leaf to reduce the effect of wind speed. The temperature difference data should be independent of the wind and light level effects. Therefore, changes in temperature difference following an irrigation event can be monitored and related to plant water status.

Preliminary results from field data indicated that leaf monitor data can be used to develop spatio-temporal crop water stress index (ST-CWSI) which has the same pattern as actual plant water stress. Data collected in almond and walnut orchards during the 2013 growing season was used to calculate ST-CWSI.

Figure 6A:
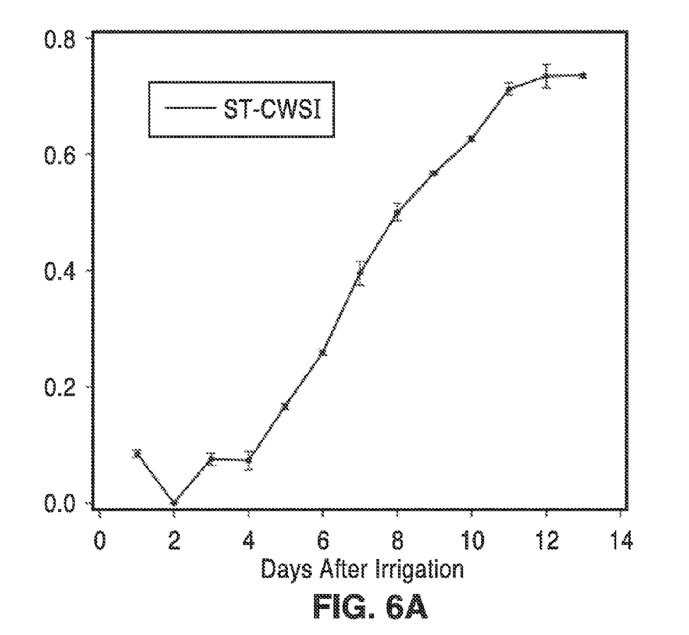
FIG. 6A is a graph of average Spatio-temporal Crop Water Stress Index (ST-CWSI) values calculated for days following irrigation of an almond tree in field conditions with standard error bars.
Figure 6B:
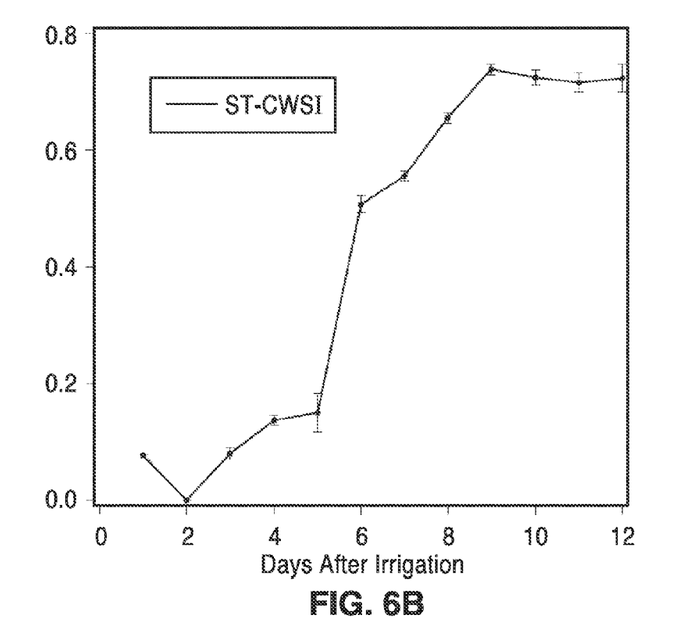
FIG. 6B is a graph of average Spatio-temporal Crop Water Stress Index (ST-CWSI) values calculated for days following irrigation of a walnut tree in field conditions with standard error bars.

FIG. 6A is a graph of ST-CWSI values calculated for days following irrigation of an almond tree in field conditions. FIG. 6B is a graph of ST-CWSI values calculated for days following irrigation of a walnut tree in field conditions. The error bars in these figures represent standard error of mean ST-CWSI. These figures clearly show the effect of plant water stress on leaf temperature following an irrigation event. ST-CWSI showed a small drop in magnitude immediately following an irrigation event (i.e. the day after irrigation) which corresponds to a high transpiration rate and then ST-CWSI increases on subsequent days as the plant water stress increases. Accordingly, information obtained by monitoring daily variations of leaf temperature as a result of changes in plant water status can be used to produce a water stress index to quantify plant water stress.

Figure 7A:
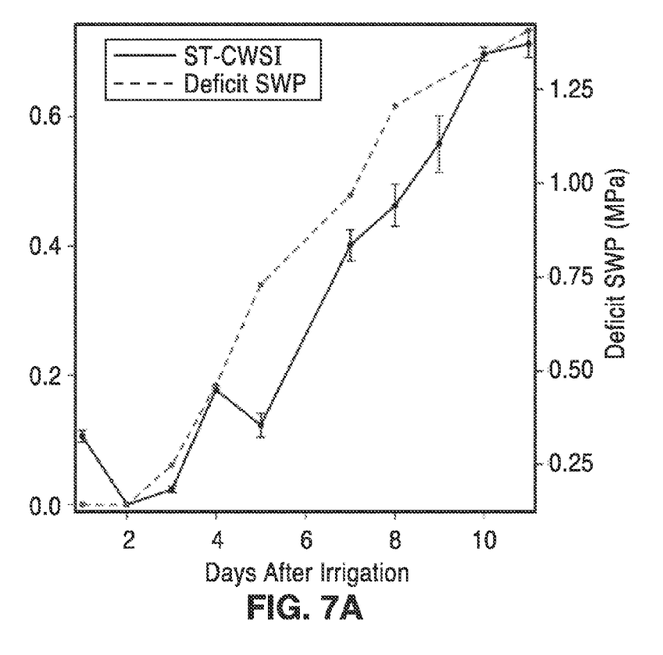
FIG. 7A is a graph of a comparison of measured deficit SWP and a Spatio-temporal Crop Water Stress Index (ST-CWSI) values calculated for days following irrigation of an almond tree in field conditions.
Figure 8A:
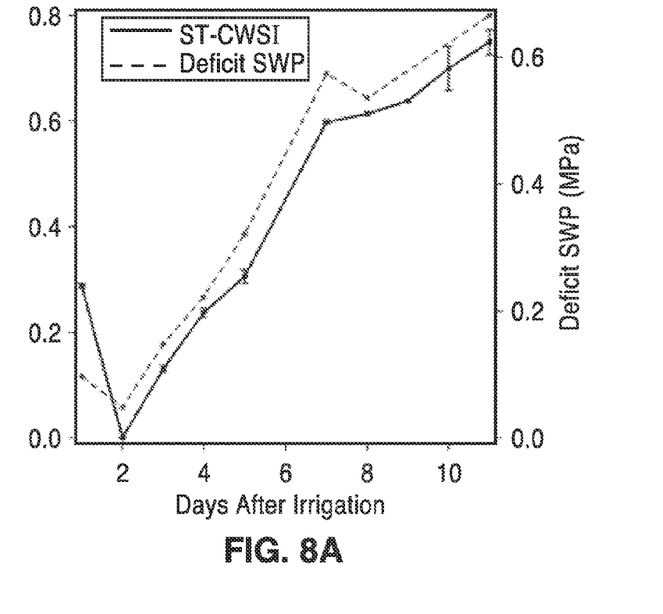
FIG. 8A is a graph of a comparison of measured deficit SWP and Spatio-temporal Crop Water Stress Index (ST-CWSI) values calculated for days following irrigation of a walnut tree in field conditions.

FIG. 7A and FIG. 8A show a comparison of calculated ST-CWSI with actual plant water stress for almond and walnut trees respectively. The daily ST-CWSI curve as compared with the curve of actual water stress level measured at mid-day following an irrigation event in almonds and in walnuts is shown in these figures. The actual plant water status was measured as ground-truth data. FIG. 7A and FIG. 8A show both ST-CWSI and DSWP (deficit SWP-DSWP was calculated by subtracting measured SWP from baseline SWP (BSWP), where BSWP represents SWP of well watered tree) curves for an irrigation event for almond and walnut trees. Similar patterns of tree recovery for the first two days after irrigation and then stress level increasing on following days can be seen in both curves.

The mid-day stem water potential (SWP) values from the tree on which leaf monitor was installed was measured using the standard "pressure chamber" approach. For this comparison, mid-day SWP was adjusted for weather conditions by calculating deficit SWP (DSWP). ST-CWSI curve was also found to be correlated well with measured mid-day SWP for both almond and walnut crops.

Figure 7B:
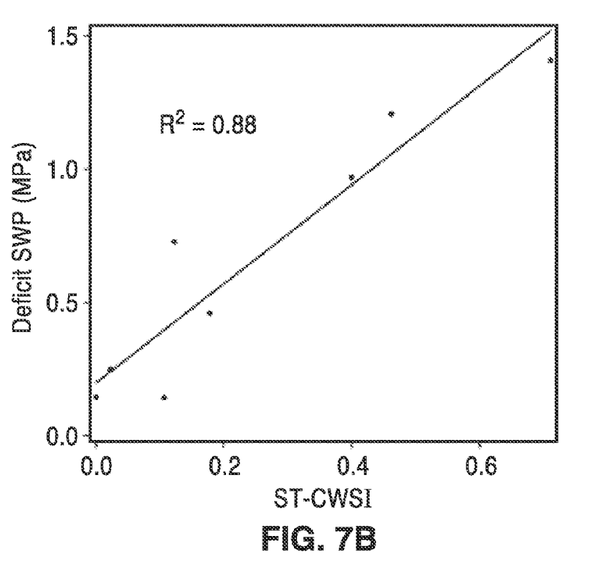
FIG. 7B is a linear regression between daily ST-CWSI and measured Deficit SWP for almonds shown in FIG. 7A.
Figure 8B:
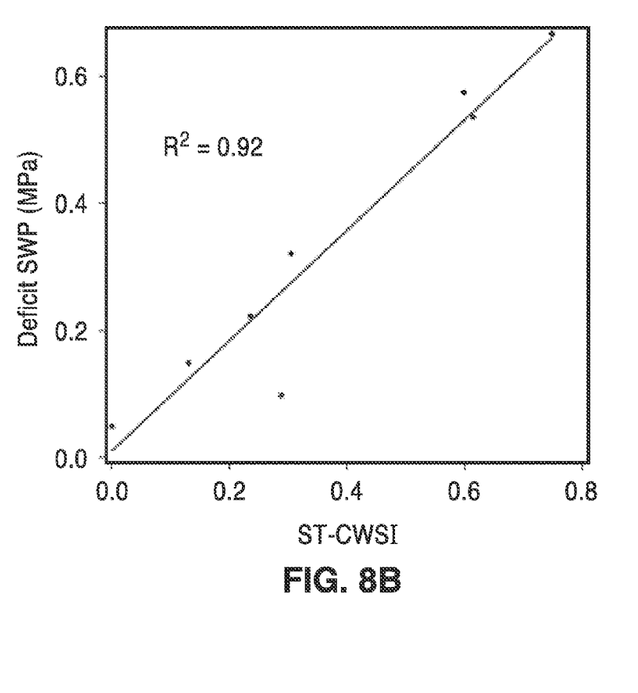
FIG. 8B is a linear regression between daily ST-CWSI and measured Deficit SWP for walnuts shown in FIG. 8A.

Linear regression between daily ST-CWSI and measured Deficit SWP for almonds is shown in FIG. 7B and in walnuts is shown in FIG. 8B. The measured DSWP was regressed on estimated ST-CWSI for these irrigation events. Coefficient determinations of 0.88 and 0.92 were found for almond and walnut trees respectively. Table 1 shows linear regression results for different irrigation events for other trees. The table shows results for simple linear regression of ST-CWSI on measured mid-day deficit SWP for different irrigation events for almond and walnut trees during the 2013 growing season. Overall, ST-CWSI was able to predict DSWP with high $R^2$ for most of the trees. Relatively lower $R^2$ values in October could be because of relatively cold and humid environment present at that time and the onset of leaf senescing during that period.

From the description herein, it will be appreciated that that the present disclosure encompasses multiple embodiments which include, but are not limited to, the following:

1. An apparatus for monitoring plant leaves to determine plant water needs, comprising: (a) a sensor platform; (b) a suite of sensors coupled to the sensor platform, comprising: (i) at least one leaf temperature sensor for measuring leaf temperatures over time, (ii) an air temperature sensor; (iii) a relative humidity sensor adapted to measuring relative humidity surrounding a leaf; and (iv) an ambient light sensor configured for measuring levels of solar radiation on the leaf; (c) a platform computer processor configured for receiving measurement information from the sensor suite; and (d) programming executable on said processor for determining plant water status (PWS) in response to monitoring environmental parameters in the vicinity of the leaf.

2. An apparatus as recited in any previous embodiment, wherein the sensor platform further comprises a plurality of wind speed sensors configured for measuring wind speed surrounding a leaf.

3. An apparatus as recited in any previous embodiment, wherein the programming further comprises filtering data from the sensor suite to utilize only data corresponding to wind speeds below a given threshold value.

4. An apparatus as recited in any previous embodiment, wherein the sensor platform further comprises a wind barrier configured for suppressing effects of wind speed on leaf transpiration.

5. An apparatus as recited in any previous embodiment, wherein the wind speed sensors are positioned inside and outside of the wind barrier to detect and verify effectiveness of the wind barrier.

6. An apparatus as recited in any previous embodiment, wherein the sensor platform further comprises a leaf retainer adapted to orient a leaf surface with the suite of sensors.

7. An apparatus as recited in any previous embodiment, wherein the sensor platform further comprises a solar radiation diffuser to provide a uniform light level exposure upon the leaf.

8. An apparatus as recited in any previous embodiment, further comprising: a plurality of irrigation valve stations with selectively energizeable valves that are opened or closed upon activation or deactivation to control water flow through the valves; and programming executable on the processor for controlling frequency and duration of irrigation valve opening or dosing by sending a series of control signals to the irrigation valves based on determined plant water status.

9. An apparatus as recited in any previous embodiment, further comprising: a field transceiver operably coupled to the platform computer processor of the sensor platform; a central control system with a control computer processor, a user interface and central control transceiver; programming executable on said control computer processor for transmitting sensor data and control signals between the control and platform computer processors through the control and field transceivers.

10. A system for monitoring plant leaves to determine plant water needs, the system comprising: (a) a plurality of field sensor platforms, each platform comprising: (i) a suite of sensors monitoring environmental conditions surrounding at least one leaf; (ii) a power supply; and (iii) a field platform transceiver; (b) a central controller with a control computer processor, user interface, and a central control transceiver, the control computer processor configured for receiving sensor measurement information from each sensor suite through the field platform and field control transceivers; (c) programming executable on said control processor for transmitting and receiving signals between the central controller and each field sensor platform; and (d) programming executable on said control processor for determining plant water status (PWS) based on sensor measurement information transmitted and received from each field sensor platform.

11. A system as recited in any previous embodiment, wherein the suite of sensors of each field sensor platform, comprises: (a) at least one leaf temperature sensor for measuring leaf temperatures over time; (b) an air temperature sensor; (c) a relative humidity sensor adapted to measuring relative humidity surrounding a leaf; (d) a wind speed sensor configured for measuring wind speed surrounding a leaf; and (e) an ambient light sensor configured for measuring levels of solar radiation on the leaf.

12. A system as recited in any previous embodiment, wherein the sensor platform further comprises a leaf retainer adapted to orient a leaf surface with the suite of sensors.

13. A system as recited in any previous embodiment, wherein the sensor platform further comprises a solar radiation diffuser to provide a uniform light level exposure upon the leaf.

14. A system apparatus as recited in any previous embodiment, wherein the sensor platform further comprises a wind barrier configured for suppressing effects of wind speed on leaf transpiration.

15. A system apparatus as recited in any previous embodiment, wherein the power supply comprises batteries and a solar charger.

16. A system as recited in any previous embodiment, further comprising: a plurality of irrigation valve stations with selectively energizeable valves that are opened or closed upon activation or deactivation to control water flow through the valves; and programming executable on the control processor for controlling frequency and duration of irrigation valve opening or dosing by sending a series of control signals to the irrigation valves based on determined plant water status of each plant.

17. A method for determining plant water needs, comprising: acquiring leaf temperature, air temperature, ambient light, relative humidity and wind speed sensor measurements of a selected leaf over a time period; determining differences between measurements over the time period; calculating crop water stress index values from sensor measurement differences periodically; and determining plant water status from the calculated crop water stress index values.

18. A method as recited in any previous embodiment, further comprising: filtering acquired sensor data to measurements to use measurements that are acquired when wind speed is below a selected level and ambient light is above a selected level.

19. A method as recited in any previous embodiment, wherein the differences between measurements are determined by comparing current measurements with measurements taken the day after irrigation of the plant.

20. The method as recited in any previous embodiment, further comprising: comparing calculated spatio-temporal crop water stress index values with recommended crop water stress index values; and initiating a watering event when the calculated crop water stress index value exceeds the recommended crop water stress index value.

21. The method as recited in any previous embodiment, wherein the programming further comprises filtering and smoothing data from the sensor suite to utilize only data corresponding to a particular time window.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| Crop | Tree | Month | RMSE | R² |
|---|---|---|---|---|
| Almond | 1 | August | 0.11 | 0.73 |
| Almond | 2 | August | 0.19 | 0.84 |
| Almond | 3 | August | 0.19 | 0.5 |
| Almond | 4 | August | 0.09 | 0.88 |
| Almond | 4 | October | 0.11 | 0.69 |
| Walnut | 1 | August | 0.05 | 0.45 |
| Walnut | 2 | August | 0.1 | 0.59 |
| Walnut | 3 | August | 0.08 | 0.92 |
| Walnut | 4 | August | 0.13 | 0.55 |
| Walnut | 5 | October | 0.14 | 0.61 |

What is claimed is:

1. An apparatus for monitoring plant leaves to determine plant water needs, comprising:
   (a) a sensor platform;
   (b) a suite of sensors coupled to the sensor platform, comprising:
      (i) at least one leaf temperature sensor for measuring leaf temperatures over time;
      (ii) an air temperature sensor;
      (iii) a relative humidity sensor adapted to measuring relative humidity surrounding a leaf;
      (iv) an ambient light sensor configured for measuring levels of solar radiation on the leaf; and
      (v) one or more wind speed sensors configured for measuring wind speed surrounding a leaf;
   (c) a platform computer processor configured for receiving measurement information from the suite of sensors; and
   (d) programming executable on said processor for determining plant water status (PWS) in response to monitoring environmental parameters in the vicinity of the leaf,
   wherein said programming further comprises filtering data from said sensor suite to utilize only data corresponding to wind speeds below a given threshold value.

2. The apparatus as recited in claim 1, wherein said sensor platform further comprises a wind barrier configured for suppressing effects of wind speed on leaf transpiration.

3. The apparatus as recited in claim 2, wherein said wind speed sensors are positioned inside and outside of said wind barrier to detect and verify effectiveness of said wind barrier.

4. The apparatus as recited in claim 1, wherein said sensor platform further comprises a leaf retainer adapted to orient a leaf surface with said suite of sensors.

5. The apparatus as recited in claim 1, wherein said sensor platform further comprises a solar radiation diffuser to provide a uniform light level exposure upon the leaf.

6. The apparatus as recited in claim 1, further comprising:
   a plurality of irrigation valve stations with selectively energizeable valves that are opened or closed upon activation or deactivation to control water flow through the valves; and
   programming executable on said processor for controlling frequency and duration of irrigation valve opening or closing by sending a series of control signals to the irrigation valves based on determined plant water status.

7. The apparatus as recited in claim 1, further comprising:
   a field transceiver operably coupled to the platform computer processor of the sensor platform;
   a central control system with a control computer processor, user interface and central control transceiver; and
   programming executable on said control computer processor for transmitting sensor data and control signals between the control and platform computer processors through the control and field transceivers.

8. A system for monitoring plant leaves to determine plant water needs, the system comprising:
   (a) a plurality of field sensor platforms, each platform comprising:
      (i) a suite of sensors monitoring environmental conditions surrounding at least one leaf;
      (ii) a power supply;
      (iii) a field platform transceiver; and
      (iv) a leaf retainer adapted to orient a leaf surface with said suite of sensors;
   (b) a central controller with a control computer processor, user interface, and a central control transceiver, the control computer processor configured for receiving sensor measurement information from each sensor suite through the field platform transceiver and the central control transceiver;

(c) programming executable on said control processor for transmitting and receiving signals between the central controller and each field sensor platform; and (d) programming executable on said control processor for determining plant water status (PWS) based on sensor measurement information transmitted and received from each field sensor platform.

9. The system as recited in claim 8, wherein said suite of sensors of each field sensor platform, comprises:
(a) at least one leaf temperature sensor for measuring leaf temperatures over time;
(b) an air temperature sensor;
(c) a relative humidity sensor adapted to measuring relative humidity surrounding a leaf;
(d) a wind speed sensor configured for measuring wind speed surrounding a leaf; and
(e) an ambient light sensor configured for measuring levels of solar radiation on the leaf.

10. The system as recited in claim 8, wherein each of said sensor platforms further comprise a solar radiation diffuser to provide a uniform light level exposure upon the leaf.

11. The system as recited in claim 8, wherein each of said sensor platforms further comprise a wind barrier configured for suppressing effects of wind speed on leaf transpiration.

12. The system as recited in claim 8, wherein said power supply comprises batteries and a solar charger.

13. The system as recited in claim 8, further comprising:
a plurality of irrigation valve stations with selectively energizeable valves that are opened or closed upon activation or deactivation to control water flow through the valves; and
programming executable on said control processor for controlling frequency and duration of irrigation valve opening or closing by sending a series of control signals to the irrigation valves based on determined plant water status of each plant.

14. A method for determining plant water needs, comprising:
acquiring leaf temperature, air temperature, ambient light, relative humidity and wind speed sensor measurements of a selected leaf over a time period;
determining differences between measurements over the time period;
calculating crop water stress index values from sensor measurement differences periodically;
comparing calculated spatio-temporal crop water stress index values with recommended crop water stress index values;
determining plant water status from the calculated crop water stress index values; and
initiating a watering event when the calculated crop water stress index value exceeds the recommended crop water stress index value.

15. The method as recited in claim 14, further comprising:
filtering acquired sensor data to measurements to use measurements that are acquired when wind speed is below a selected level and ambient light is above a selected level.

16. The method as recited in claim 14, wherein said differences between measurements are determined by comparing current measurements with measurements taken the day after irrigation of the plant.

17. A system for monitoring plant leaves to determine plant water needs, the system comprising:
(a) a plurality of field sensor platforms, each platform comprising:
(i) a suite of sensors monitoring environmental conditions surrounding at least one leaf;
(ii) a power supply;
(iii) a field platform transceiver; and
(iv) a solar radiation diffuser to provide a uniform light level exposure upon the leaf;
(b) a central controller with a control computer processor, user interface, and a central control transceiver, the control computer processor configured for receiving sensor measurement information from each sensor suite through the field platform transceiver and the central control transceiver;
(c) programming executable on said control processor for transmitting and receiving signals between the central controller and each field sensor platform; and
(d) programming executable on said control processor for determining plant water status (PWS) based on sensor measurement information transmitted and received from each field sensor platform.

18. The system as recited in claim 17, wherein said sensor platform further comprises a leaf retainer adapted to orient a leaf surface with said suite of sensors.

19. The system as recited in claim 17, wherein each of said sensor platforms further comprise a wind barrier configured for suppressing effects of wind speed on leaf transpiration.

20. The system as recited in claim 17, further comprising:
a plurality of irrigation valve stations with selectively energizeable valves that are opened or closed upon activation or deactivation to control water flow through the valves; and
programming executable on said control processor for controlling frequency and duration of irrigation valve opening or closing by sending a series of control signals to the irrigation valves based on determined plant water status of each plant.

21. An apparatus for monitoring plant leaves to determine plant water needs, comprising:
(a) a sensor platform with a wind barrier configured for suppressing effects of wind speed on leaf transpiration;
(b) a suite of sensors coupled to the sensor platform, comprising:
(i) at least one leaf temperature sensor for measuring leaf temperatures over time;
(ii) an air temperature sensor;
(iii) a relative humidity sensor adapted to measuring relative humidity surrounding a leaf;
(iv) an ambient light sensor configured for measuring levels of solar radiation on the leaf; and
(v) a plurality of wind speed sensors configured for measuring wind speed surrounding a leaf, said wind speed sensors positioned inside and outside of the wind barrier to detect and verify effectiveness of the wind barrier;
(c) a platform computer processor configured for receiving measurement information from the sensor suite; and
(d) programming executable on said processor for determining plant water status (PWS) in response to monitoring environmental parameters in the vicinity of the leaf.

22. The apparatus as recited in claim 21, wherein said programming further comprises filtering data from said sensor suite to utilize only data corresponding to wind speeds below a given threshold value.

23. The apparatus as recited in claim 21, wherein said sensor platform further comprises a leaf retainer adapted to orient a leaf surface with said suite of sensors.

24. The apparatus as recited in claim 21, wherein said sensor platform further comprises a solar radiation diffuser to provide a uniform light level exposure upon the leaf.

25. The apparatus as recited in claim 21, further comprising:
- a plurality of irrigation valve stations with selectively energizeable valves that are opened or closed upon activation or deactivation to control water flow through the valves; and
- programming executable on said processor for controlling frequency and duration of irrigation valve opening or closing by sending a series of control signals to the irrigation valves based on determined plant water status.

26. A method for determining plant water needs, comprising:
- acquiring leaf temperature, air temperature, ambient light, relative humidity and wind speed sensor measurements of a selected leaf over a time period;
- filtering acquired sensor data to measurements to use measurements that are acquired when wind speed is below a selected level and ambient light is above a selected level;
- determining differences between measurements over the time period;
- calculating crop water stress index values from sensor measurement differences periodically; and
- determining plant water status from the calculated crop water stress index values.

27. The method as recited in claim 26, wherein said differences between measurements are determined by comparing current measurements with measurements taken the day after irrigation of the plant.

28. The method as recited in claim 26, further comprising:
- comparing calculated spatio-temporal crop water stress index values with recommended crop water stress index values; and
- initiating a watering event when the calculated crop water stress index value exceeds the recommended crop water stress index value.

* * * * *